United States Patent [19]

Sicek et al.

[11] Patent Number: 5,013,018

[45] Date of Patent: May 7, 1991

[54] TABLE POSITIONING FOR X-RAY EXAMINATIONS IN PLURALITY OF POSITIONS

[76] Inventors: Bernard W. Sicek; Aldona A. Siczek, both of 1252 Chinook Way, Boulder, Colo. 80303

[21] Appl. No.: 370,193

[22] Filed: Jun. 22, 1989

[51] Int. Cl.⁵ .............................................. A61G 13/00
[52] U.S. Cl. ..................................... 269/323; 378/209
[58] Field of Search ................................ 269/322–325, 269/71, 61; 378/195, 196, 209, 208, 177, 179

[56] References Cited

U.S. PATENT DOCUMENTS 4,101,120 7/1978 Seshima ............................ 269/323

Primary Examiner—Robert C. Watson

[57] ABSTRACT

A table positioner which provides total imaging coverage of the patient in horizontal, vertical and in tilt positions is disclosed for use in X-ray diagnostic examinations. The table positioner is constructed from modules which modules, depending on a particular examination procedure, are assembled together so as to provide necessary positioning. Further, this modular table positioner is compact enough to be installed in a small room or a mobile van.

1 Claim, 3 Drawing Sheets

TABLE POSITIONING FOR X-RAY EXAMINATIONS IN PLURALITY OF POSITIONS

FIELD OF THE INVENTION

This invention relates to a table positoner for use with X-ray diagnostic equipment, and, more particularly, relates to a modular table positioner providing total imaging coverage of the patient in horizontal, vertical and tilt positions.

BACKGROUND OF INVENTION

The use of a table for positioning a patient in order to effect diagnostic examinations and/or surgical treatment is well known. However, improvements in such tables are deemed to be useful for at least some applications. In particular, now known tables failed to provide adequate imaging coverage of a patient undergoing cardiac and/or vascular treatments, and more particularly, have limited coverage in small room installations, have not allowed for examinations in tilt positions when used in conjunction with cardiac/vascular C-arm devices.

SUMMARY OF INVENTION

This invention provides an improved table positioning system for use in a X-ray diagnostic examination constructed from modules. This modular construction allows to assemble a table from selected modules so that, depending on requirements of a particular examination or treatment, necessary positioning is provided (which positioning includes examinations in a tilt, horizontal and vertical positions) with total imaging coverage of the patient and better access to said patient without undue complexity or cost.

It is therefore an object of this invention to provide a table positioner of modular construction for X-ray examinations in a plurality of positioning, which construction allows to reduce the production inventory and cost.

It is still another object of this invention to provide an improved positioning system which enables examinations in a horizontal and in a substantial range of tilt positions with total imaging coverage of the patient and substantially unobstructed access to said patient and yet simply constructed at a reduced cost.

It is still another object of this invention to provide an improved table positioning system which table is lengthwise displaceable in all (including tilt) positions.

It is still another object of this invention to provide an improved table positioning system providing full imaging coverage and yet being compact.

It is still another object of this invention to provide an improved table positioning having a table top supported at one side only to assure substantially unobstructed passage under the table top for a device carrying an X-ray image source and image receptor.

It is still another objective of this invention to provide an improved table positioning system which allows for tilting the table top at substantially lower table elevation by having a pivot point close to the mid section of the patient.

With all these and other objects in view, which will become apparent to one skilled in the art as the description proceeds, this invention resides in the novel construction, combination, and arrangement of parts as hereinafter described, and more particularly defined by the appended claims, it being understood that changes in the precise embodiment of the herein disclosed invention are meant to be included as come within the scope of the claims.

BRIEF DESCRIPTION OF THE FIGURES

The present invention may be described with a greater clarity by referring following figures.

DESCRIPTION OF THE ILLUSTRATED EMBODIMENTS

The accompanying drawings illustrate a presently preferred embodiment of the invention according to the mode so far devised for the practical application of the principles thereof.

Figure 1:
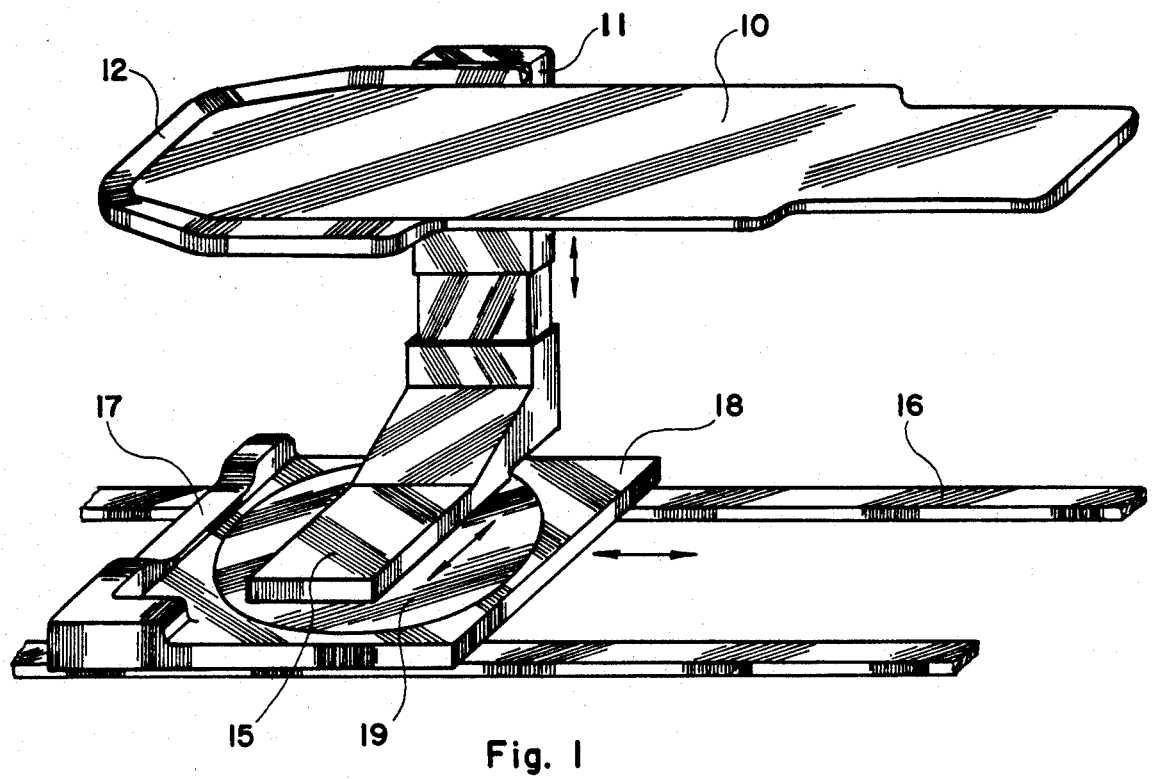
FIG. 1 is an isometric view of a modular table positioning system.

FIG. 1 is an isometric view of a modular table positioning system constructed in accordance with the principles of the present invention. This table positioning system comprises a patient supporting table top 10 (mounted in a frame 12), that is secured in an overhanging relationship to a support means 11 of telescoping construction providing a relative movement therebetween in a vertical direction wherein the support means 11 are slideably mounted on a structure 15 and slidable in a transverse direction generally perpendicular to the vertical direction, a rotary base 19 having the structure 15 mounted thereon and supported by a base support 18 in a rotatable arrangement about an axis generally parallel to the vertical direction, wherein the base support 18 is moveably mounted on four rollers resting on a rail system 16 (secured to the floor) and carries a drive means 17 for displacement of the base support in a longitudinal directions.

Figure 2:
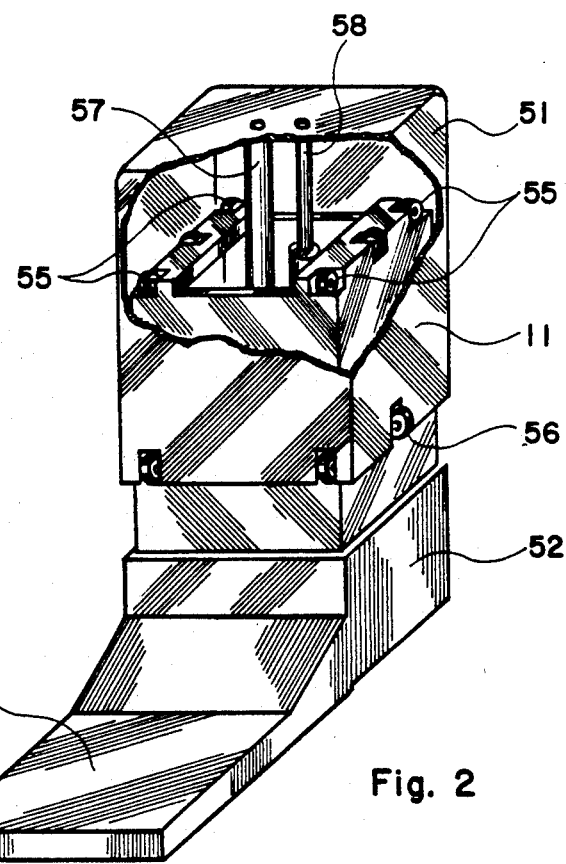
FIG. 2 illustrates the support means.

FIG. 2 illustrates in some detail the support means 11 comprising an outer structure 51 having rollers mounted on the lower portion thereof and an inner structure 52 having rollers mounted on the upper portion thereof, an actuator 58 providing a movement of the outer structure relative to the inner structure and a pneumatic spring counter balancing part of the weight of the structures being displaced.

Figure 3:
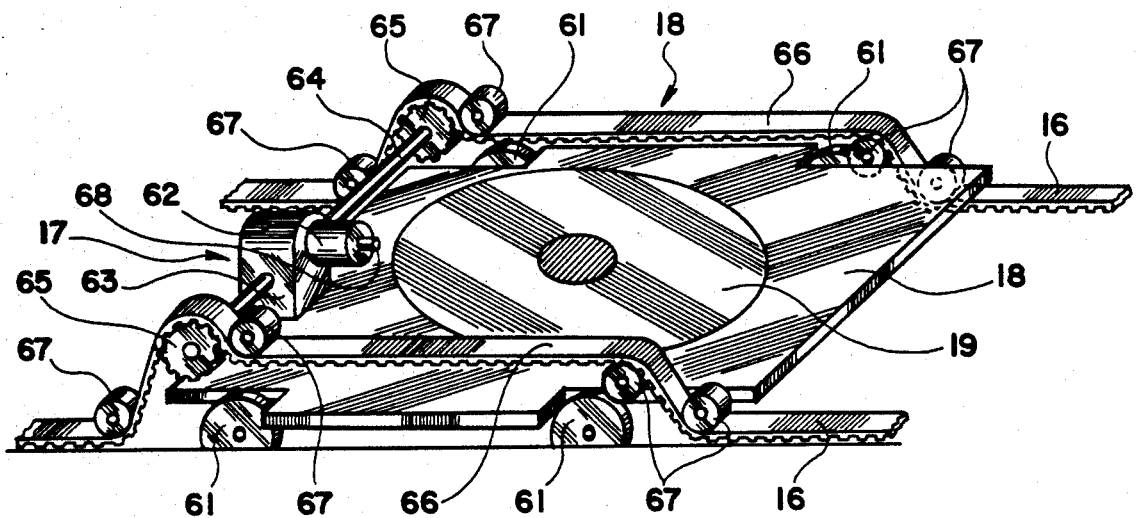
FIG. 3 illustrates, the drive means for displacement of the base support.

The drive means 17 as illustrated in FIG. 3 comprises a motor 62, a reducer 63 including a shaft 64 extending outwardly in opposite directions and having a timing pulleys 65 mounted on each end thereof, timing belts 66 extending over said timing pulleys and over each side of the base support being guided by rollers 67 and secured to the rails at the extremities thereof. Energization of the motor 62 imparts driving motion to the timing pulleys causing displacement of the base support in the longitudinal direction. The timing belt construction permits to determine a relative position of the base (hence the table top) by using an encoder 68 positioned on the motor 62 and provides a cover for the rails.

Figure 4:
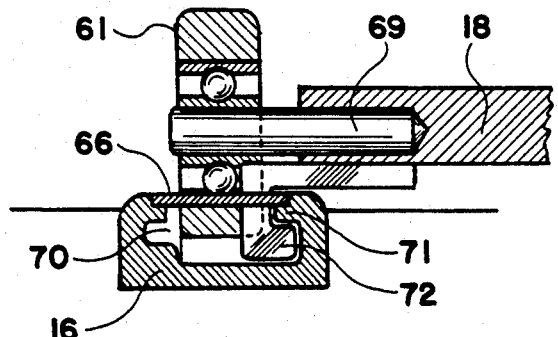
FIG. 4 is a cross section through one of the rollers supporting the base support.

A cross section through one of the roller 61 is shown in FIG. 4. The roller 61 rotatebly mounted on an axle 69 supporting the base support 18 rests on the rail 16 which rail includes a groove for receiving the timing belt 66 and further includes a flange 71 slideably engaged by a retainer member 72 affixed to the base support 18, whereby the retainer member prevents the base support 18 from separating from the rail 16 while allowing relative movement therebetween.

Figure 5:
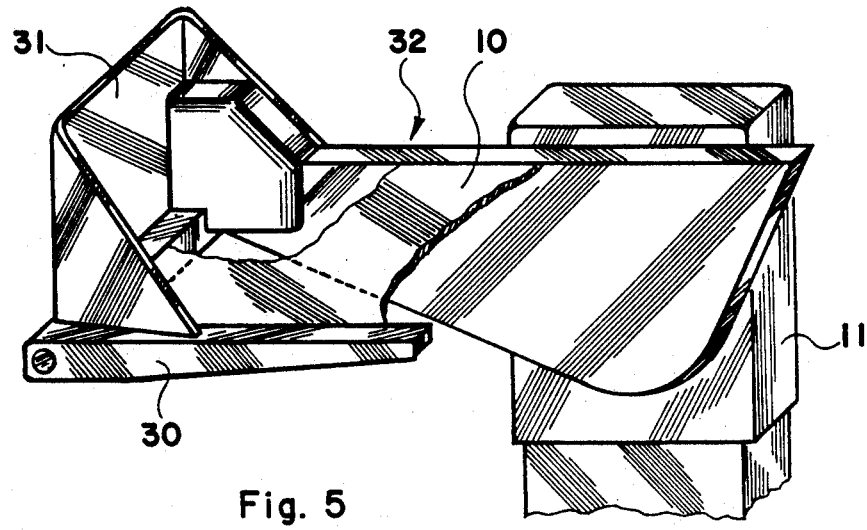
FIG. 5 illustrates still another version of the modular table positioning system with the tiltably displaceable table top.
Figure 6:
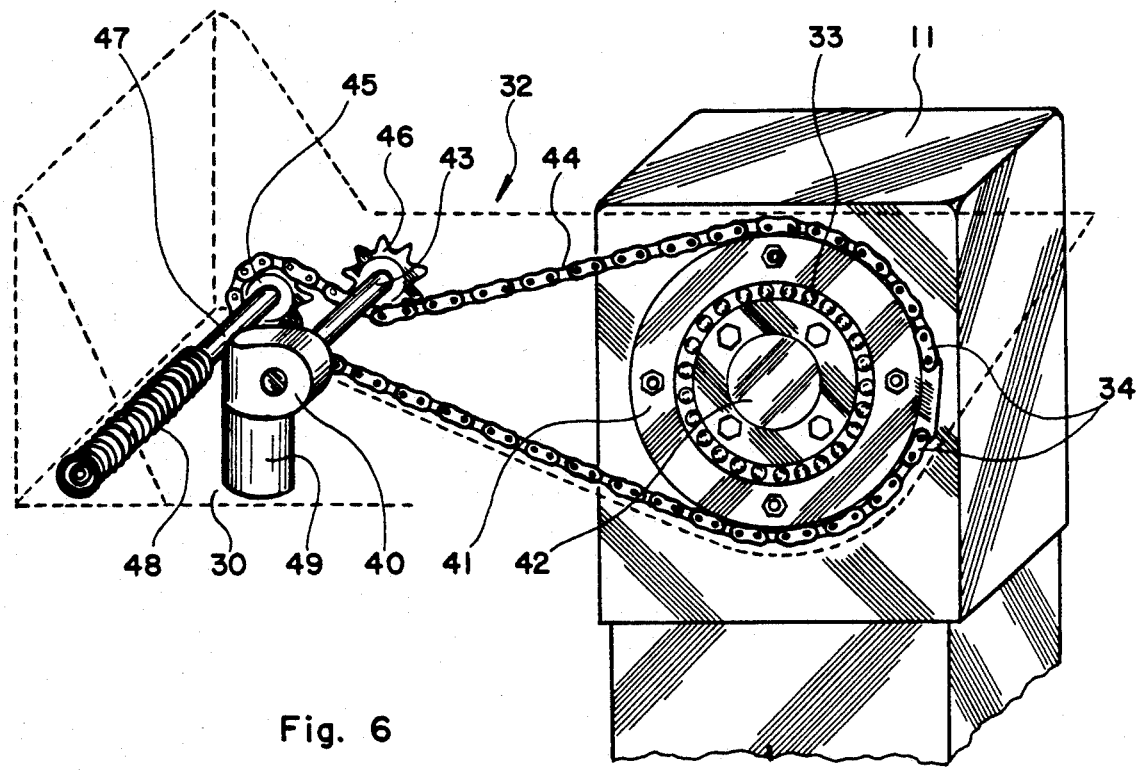
FIG. 6 illustrates the tilting mechanism for the table positioning system illustrated in FIG. 5.

Patient positioning table top 10 can be secured to support means 11 in a lengthwise slideable arrangement and also in a tiltable (about a transverse axis) arrangement. Such a tiltable arrangement is shown in FIG. 5 wherein said table top including a frame 30 (which frame includes a footrest 31) is tiltably mounted on the support means 11 and includes a tilting mechanism 32 shown in FIG. 6.

The tilting mechanism 32 comprises a bearing 33 having an outer ring 41 secured to the support means 11 and an inner ring secured to the frame 30, a chain 44 affixed to the outer ring 41 (by fasteners 34) and extending around said outer ring and around a chain sprocket 45, wherein the chain sprocket 45 is mounted on a shaft 47 secured to the frame 30 at one end and to a torsion spring 48 at the other end, which spring is affixed to the frame at its opposite end and counter balances part of the weight of the table top, a chain sprocket 46 mounted on a shaft 43 of a reducer 40 connected to a motor 49 wherein said reducer and said motor are positioned in the proximity of the footrest. Energization of the motor 49 imparts driving motion to the sprocket 46 causing said sprocket to rotate and engage with the chain providing relative tilting of the frame 30 (and hence the table top).

What is claimed is:

1. A medical examination table comprising in combination:
    a base assembly with a plurality of rollers rolling on and guided by a track installed on a floor, said base assembly supporting a columnar member vertically extending therefrom in an arrangement providing a sliding movement of said columnar member relative to said base assembly in a direction generally perpendicular to said track and a rotary movement of said columnar member relative to said base assembly about a vertical axis, said columnar member further including a securing member moveable along a vertical axis relative to said columnar member,
    a table secured in an overhanging relationship to said securing member in a pivotable arrangement about a horizontal axis,
    an actuating means included in said base assembly and comprising timing pulleys working in conjunction with timing belts secured to said track at the extremities thereof and shielding said track from dust, a drive imparting means for imparting driving motion to said timing pulleys causing displacement of said base assembly along said track.

* * * * *